US011660363B2

(12) United States Patent
McGrade

(10) Patent No.: US 11,660,363 B2
(45) Date of Patent: May 30, 2023

(54) BEVERAGE CAN SANITIZER

(71) Applicant: Michael McGrade, West Covina, CA (US)

(72) Inventor: Michael McGrade, West Covina, CA (US)

( * ) Notice: Subject to any disclaimer, the term of this patent is extended or adjusted under 35 U.S.C. 154(b) by 859 days.

(21) Appl. No.: 16/601,515

(22) Filed: Oct. 14, 2019

(65) Prior Publication Data

US 2020/0038531 A1 Feb. 6, 2020

Related U.S. Application Data

(63) Continuation-in-part of application No. 15/153,068, filed on May 12, 2016, now Pat. No. 10,501,234.

(51) Int. Cl.
| | |
|---|---|
| *A61L 2/18* | (2006.01) |
| *A61L 2/26* | (2006.01) |
| *C11D 3/48* | (2006.01) |
| *D04H 11/00* | (2006.01) |
| *C11D 17/04* | (2006.01) |
| *D04H 1/435* | (2012.01) |

(52) U.S. Cl.
CPC .................. *A61L 2/18* (2013.01); *A61L 2/26* (2013.01); *C11D 3/48* (2013.01); *C11D 17/049* (2013.01); *D04H 1/435* (2013.01); *D04H 11/00* (2013.01); *A61L 2202/23* (2013.01); *D10B 2331/04* (2013.01); *D10B 2509/00* (2013.01)

(58) Field of Classification Search
CPC ........ B65D 17/00; B65D 17/50; B65D 51/18; B65D 25/20
USPC ...................................................... 220/85 R
See application file for complete search history.

(56) References Cited

U.S. PATENT DOCUMENTS

| | | | | |
|---|---|---|---|---|
| 4,651,890 | A | * | 3/1987 | Coker .................. B65D 77/24 215/6 |
| 5,014,869 | A | | 5/1991 | Hammond |
| 5,143,241 | A | | 9/1992 | Szymanski |
| 6,015,059 | A | | 1/2000 | Takayama |
| 6,073,797 | A | | 6/2000 | Barous |
| 6,321,927 | B2 | | 11/2001 | Cavella |
| 2005/0245151 | A1 | * | 11/2005 | Annis .................. D06M 15/59 442/97 |

* cited by examiner

*Primary Examiner* — Monzer R Chorbaji
(74) *Attorney, Agent, or Firm* — Mark S Hubert

(57) ABSTRACT

A unitary, single-use, sanitary sterilizing wipe for a beverage can. It has a number of can wiping interfaces incorporated into its design that matingly conforms to a standard beverage can, and uses a natural sterilizing fluid that is frictionally wiped onto the can's outer surfaces before drinking from the can. It may be used anywhere by opening the polymer seal, removing the wipe, placing it on the top of a beverage can and twisting it under pressure to sterilize the can.

5 Claims, 3 Drawing Sheets

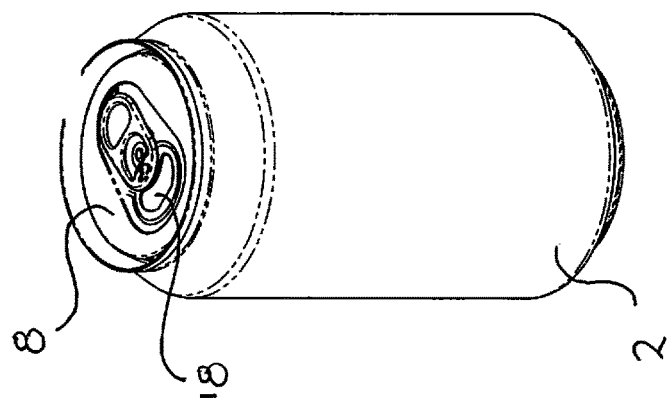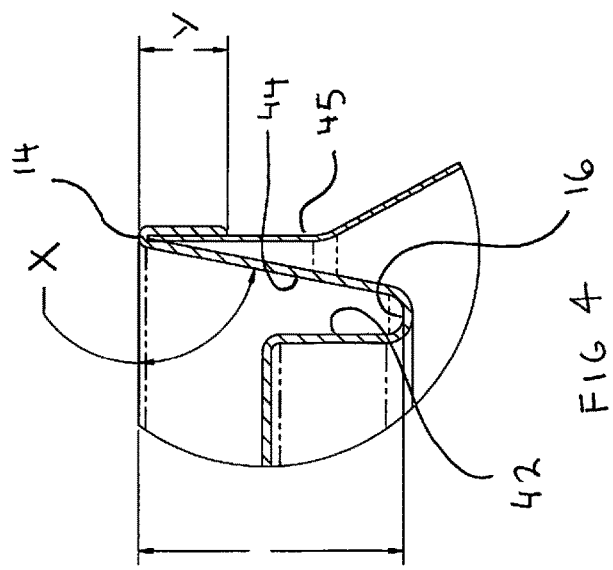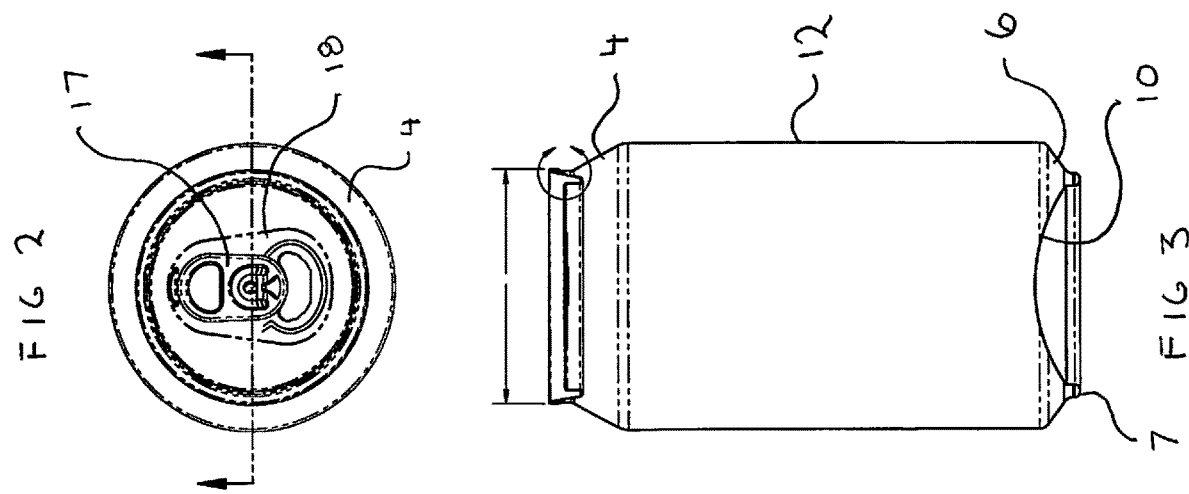

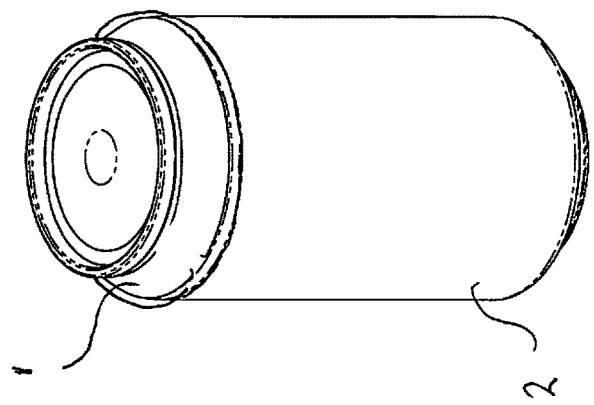
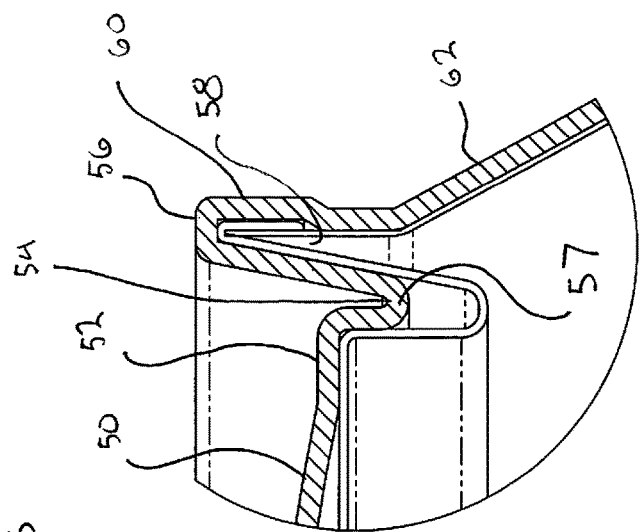
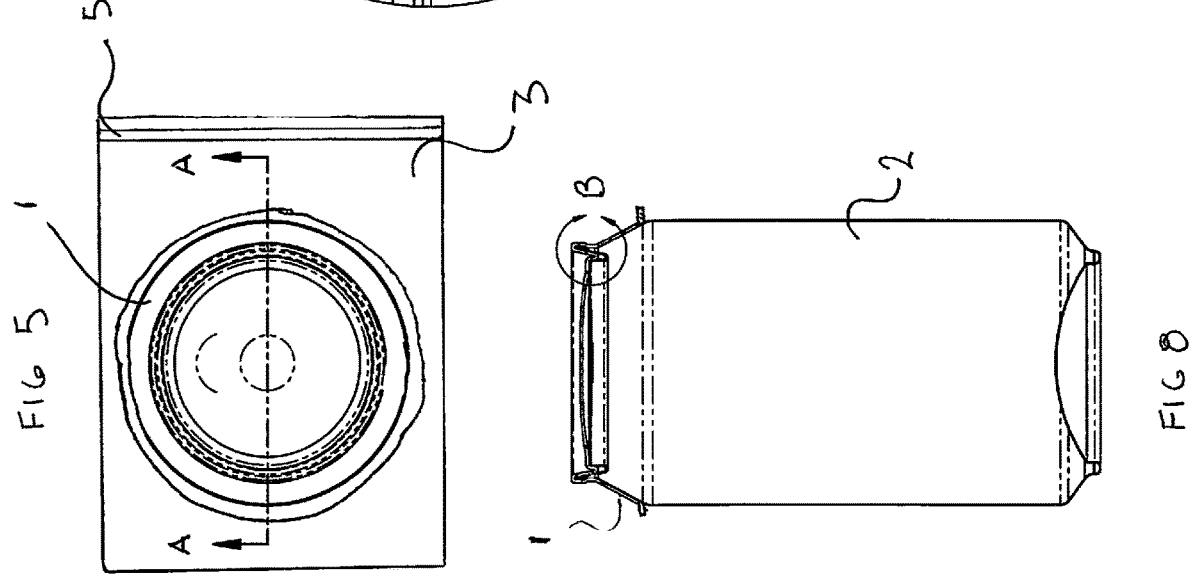

BEVERAGE CAN SANITIZER

CROSS-REFERENCE TO RELATED APPLICATIONS

THIS APPLICATION IS A CONTINUATION IN PART OF U.S. patent application Ser. No. 15/153,068 FILED May 12, 2016, ENTITLED "BEVERAGE CAN SANITARY SEAL" WHICH IS INCORPORATED BY REFERENCE HEREIN, IN ITS ENTIRETY.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to sanitary cleaners, and more particularly to single use, sanitary wipes for beverage can tops.

BACKGROUND

Pop, juice, beer and the like are generally shipped, stocked and sold naked. That is to say with their bare, aluminum or metal cans as the only barrier between the consumer and the fluid contained inside. This gives rise to the possibility of contaminants in biological, chemical and particulate form, depositing on the area of the can where the consumer either places their lips to drink, or pours the contents out into a glass.

There is a plethora of prior art sanitary wipes. These are generally simple paper fiber cloths that are soaked with a chemical cleaning and sanitizing product. They are designed to quickly evaporate as they use cleaning and sanitizing fluid combinations with a low boiling point so as to vaporize at room temperature. These are generally sold in planar sheets that are rolled and put into an airtight dispenser. The problem is that the top of a conventional beverage has a plethora of nooks and crannies that harbor debris and germs. A simple planar sheet good does not reach all of the beverage can's top. Also, since planar wipes come in rolls rather than being individually wrapped, if one wipe is contaminated, or inadequately doused with sanitizer, they all may be. Last, a sanitizer with a pH in a range adequate to remove the gum residue from a price sticker is needed.

Henceforth, an improved beverage can sanitizer that would overcome the above-mentioned failures of the prior art would fulfill a long felt need in the beverage industry. This new invention utilizes and combines known and new technologies in a unique and novel configuration to overcome the aforementioned problems and accomplish this.

BRIEF SUMMARY

In accordance with various embodiments, a sealed, single use, beverage can sanitizing wipe that has a physical configuration with multiple faces that approximates the top of a conventional beverage can, or can easily be conformed to approximate this shape, is provided.

An individually packaged, sanitizing wipe designed to contact all nooks and crannies on a conventional beverage top, that uses a natural sanitizer that does not leave any chemical residue and is safe for humans is provided.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 1 is a perspective side view of a conventional beverage can;

FIG. 2 is a top view of a conventional beverage can;

FIG. 3 is a side cross sectional view of a conventional beverage can through section A-A of FIG. 2;

FIG. 4 is a cross sectional view of a conventional beverage can showing section B of FIG. 3:

FIG. 5 is a top view of the beverage can sanitizer in its protective packaging;

FIG. 8 is a side cross sectional view of the beverage can sanitizer of a beverage can;

FIG. 9 is an enlargement of section B of FIGS. 8: and

FIG. 10 is a side perspective view of the beverage can sanitizer installed on a beverage can.

DETAILED DESCRIPTION

Figure 6:
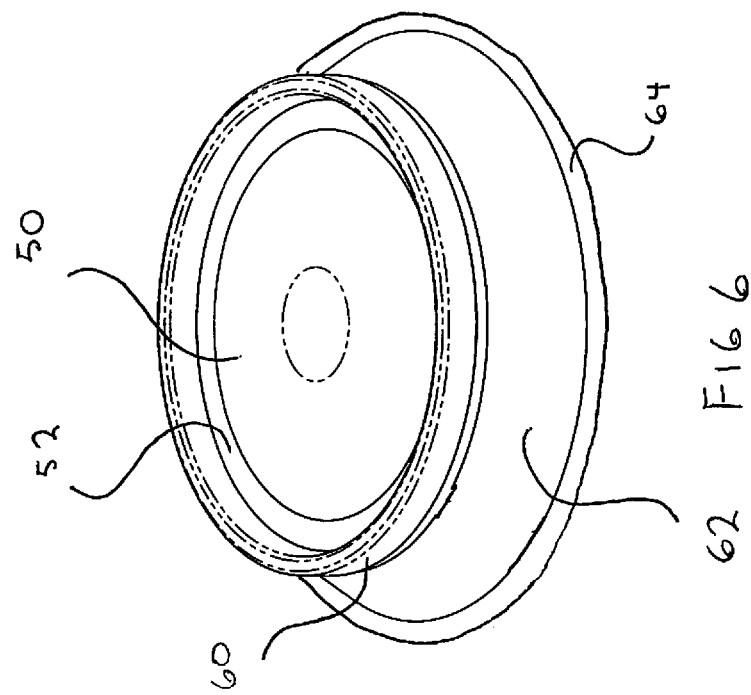
FIG. 6 is a top perspective view of the beverage can sanitizer unpackaged.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The terms "sanitizing and disinfecting" as used herein refer to the use of a chemical product that reduces the number of germs only on hard, non-porous surfaces (such as the top of a beverage can) to a level considered safe by public health standards. Generally, they kill germs on contact they when the disinfectant sits visibly wet, or "dwells," on the surface. For food service, a sanitizer/disinfector should reduce the number of germs on a surface by 99.999% within 30 seconds. Sanitizing and disinfecting do not necessarily clean dirty surfaces or remove germs. These terms are used interchangeably herein.

The term "friction fit wipe" as used herein, refers to a style of wipe or method of wiping between two objects wherein the wiping occurs by the deformation, compression or deflection of at least some of the wipe against one of objects.

The term "wiping interface" as used herein, refers to the region where the wipe and the beverage top to be sanitized are in direct physical contact with each other so as to ensure that sanitizing fluid kills or prevents the contact transfer of contaminants to humans.

The term "conventional six-pack ring" as used herein, refers to the polymer six holed lanyard that encircles the side wall of a series of six substantially similar beverage cans yet cannot pass beyond the crimp rims of the cans without deformation.

The term "natural sanitizing fluid" as used herein refers to a fluid that is naturally occurring liquid and has sanitizing properties such as sterilization or disinfection that is compatible and safe for contact with the drinking surfaces of a beverage can. Lime juice, lemon juice, essential oils (tea tree, citronella, geranium, lemongrass, orange, and patchouli), white vinegar, vodka, hydrogen peroxide, are examples of this.

The present invention relates to a novel design for a sealed, single-use, porous pre-moistened sanitizing wipe for the top of a conventional beverage can. It may be unsealed at the point of the beverage purchase and used prior to opening and consuming the beverage, or it may be left for months at a time without degradation until the cleanliness of a beverage can was questionable.

Looking at FIGS. 1-4, the physical structure of the conventional beverage can 2 is best illustrated. The can 2 is of a right circular cylindrical configuration commonly having a top end wall 8 and a spatially opposed domed bottom end wall 10 bounded by bottom ring 7. Transitioning between the right circular cylindrical region 12 and the end walls is an axially inward tapered, upper skit 4 with an upper band 45, and a shorter, axially inward tapered, lower skirt 6. The bottom end wall 10 and right cylindrical regions 12 of the can (or the tapered lower skirt 6, if so provided) are commonly formed from a single piece of aluminum, tin or steel although they may be formed from two conjoined separate pieces. The top end wall 8 is a separate piece wherein the outer periphery of the top end wall 8 and the outer periphery of the right cylindrical regions 12 of the can (or the tapered upper skirt 4, if so provided) are mechanically compressed (crimped) together into a crimp rim 14, which is surrounded by a rim gutter 16 (with a short inner gutter side wall 42 and a long outer gutter side wall 44). The rim gutter 16 forms a trough around the generally planar remainder of the top end wall 8. In the central region of the top end wall 8, there is a pull tab 17 that hingedly opens a door 18 into the enclosed volume of the can 2. The pull tab 17 resides atop the upper face of the top end wall 8. The angle between the long, outer gutter side wall 44 of the rim gutter 16 and the plane of the top end wall 8 (designated as angle X) generally is 79 degrees. The length of the crimped region (designated as length Y) generally is 0.100 inches.

From FIGS. 3 and 4 it can be seen that there are eight distinct faces (including edges) of a conventional beverage can that must be contacted with a sanitizing fluid. Beginning from the bottom up these are; the upper skirt 4, the upper band 45, crimp ring 14, outer gutter side wall 44, the rim gutter 16, inner gutter side wall 42, the top end wall 8, and the top surface of the pull tab/door 17/18. These eight faces at the top of the beverage can, are all able to be reached with the six contact faces of the wipe 1 to swipe and deposit sanitizing fluid.

Looking at FIG. 5 the exterior view of the beverage can sanitizer 1 ("wipe") can best be seen. There is a resealable polymer air-tight wrapper 3 in which the wipe is encased. This can be made of any of a host of foil or polymer film products commonly used in the packaging industry including but not limited to aluminum, polypropylene, polyvinylchloride and polyethylene. It may or may not be transparent. It preferably will have a press-actuated resealabe closure 5 formed about one of its ends. Although illustrated in the preferred embodiment as individually wrapped in a non-form fitting polymer, it is envisioned that alternate embodiments may use a thicker, resealable air-tight bag that functions as a humidor and houses a stacked array of numerous wipes with or without a humidifier (such as a sanitizer-soaked sponge) therein.

Figure 7:
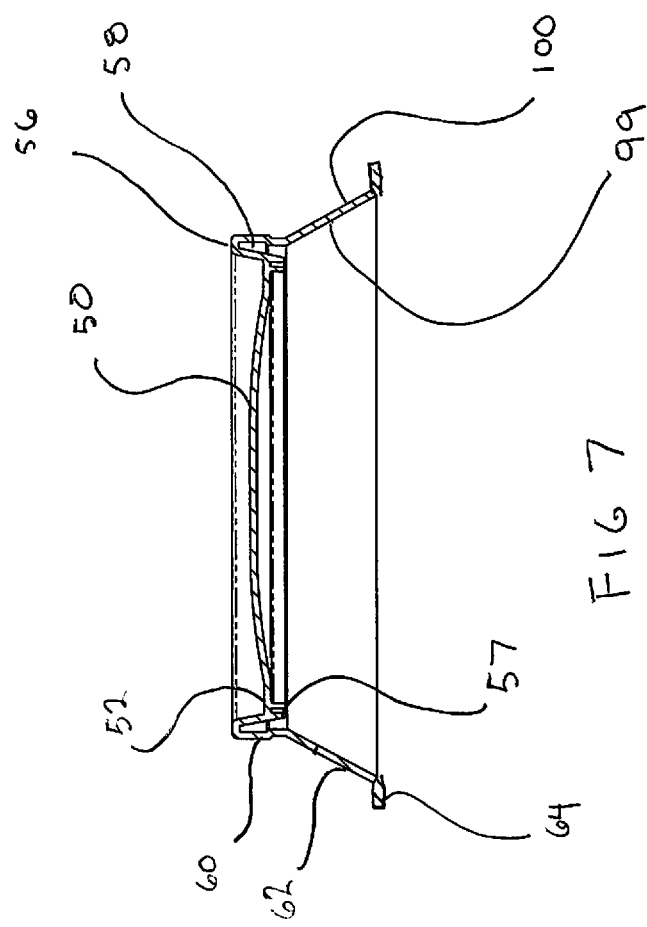
FIG. 7 is a cross sectional view of the beverage can sanitizer taken through section lines A-A of FIG. 5.

Looking at FIGS. 6-10 the design and structure of the beverage can sanitizer ("wipe") 1 can best be seen. It is made of a single piece, porous, non-woven filament fiber that is softened through agitation and chemistry with spun polyester as the preferred option. The specific polyester may be selected from the group of polyesters comprising natural polyesters, synthetic polyesters or polyester blends. These include polyethylene terephthalate (PET), telechelic oligomers; polycaprolactone diol (PCL), polyethylene adipate diol (PEA), and cotton-polyester blends (Polycot). Polyester was chosen because spun polyester is much softer and absorbent (ad-sorbs) than filament. This absorbent characteristic in important for dousing the wipe 1 with the sanitizer.

The wipe 1 is obtained in a planar sheet format and heat and vacuum formed to make the double pleat, the dome, the lower flared sidewall and bottom flange into its three-dimensional form. The sanitizer/disinfectant is preferably sprayed over the brushed bottom of the wipe 1, although in alternate embodiments the wipe 1 may be soaked to absorb the fluid so as to saturate or coat the wipe 1. Depending on the degree of wetess, the wipe 1 may be partially dried before sealing.

There is a polymer air-tight wrapper (seal bag) 3 in which the wipe is encased. This can be made of any of a host of foil or polymer film products commonly used in the packaging industry including but not limited to aluminum, polypropylene, polyvinylchloride and polyethylene. It may or may not be transparent. Although illustrated in the preferred embodiment as individually wrapped in a non-form fitting resealable polymer bag, it is envisioned that alternate embodiments may use a thicker, resealable air-tight bag that functions as a humidor and houses a stacked array of numerous wipes 1 with or without a humidifier (such as a sanitizer-soaked sponge) therein. To ensure that there is no degradation of whatever sanitizer is used while it sits in its seal bag 3, the wipe 1 may be sealed in its seal bag 3 under an inert atmosphere or it may be sealed in the atmosphere and passed through a gamma irradiator to undergo gamma irradiation (I.E. from a Co$^{60}$ source) to destroy any bacteria in the sealed bag.

The wipe has two faces, and outer face 99 and an inner face 100. The inner face 99 has a brushed surface such that the polyester fibers are raised slightly making for a softer feel and a better trap for the retention of the sanitizing fluid. While spun polyester is long-lasting in wear-life, it is softer and can actually resemble cotton. However, there are other material equivalents that are well known in the industry and could be substituted.

The wipe 1 is constructed in a non-planar circular disk configuration with a single, central dome 50 having a peripheral ring 52 that bends at approximately 90 degrees and becomes the lower pleat fold 54 of a double pleat. The dome 50 has sufficient vertical lift to clear the pull-tab 17. The lower pleat fold 54 approximates the angle found between the outer gutter side wall 44 and the inner gutter side wall 42 at the rim gutter 16. At the bottom of the lower pleat fold is a rolled bottom edge 57. There is a rolled top edge 56 that defines the upper pleat fold 58. The upper pleat fold approximates the angle found between the outer gutter side wall 44 and the upper band 45. The rolled top edge 56 is the highest point of the wipe 1 and it returns into the upper sidewall 60 which forms into the lower flared sidewall 62 and bottom flange 64. The lower flared sidewall shares the same angle as the upper skirt 4. (Designated as X in FIG. 4.)

Here, it can be seen that the wipe 1 has a total of six distinct but contiguous inner contact faces formed by head and vacuum to wipe sanitizing fluid onto the top of a beverage can. They are: the central dome 50, the peripheral ring 52, the lower pleat fold 54, the upper pleat fold 58, the upper sidewall 60, and the lower flared sidewall 62.

To use, the protective seal bag 3 is opened and the wipe 1 checked for moistness (to ensure that there has not been a breach of the protective wrapper that has partially or fully evaporated the disinfectant/sanitizer). The top end wall 8 of the can 2 is then blown free of dirt and loose debris. Hereinafter, there are three wipe steps to sanitize the can. The double pleat of the wipe 1 is aligned on the beverage can 2 such that the lower rolled edge 57 of the lower pleat fold 54 sits in the rim gutter 16 and the inside of the upper pleat fold 58 is over the crimp ring 14. This allows for a friction fit wipe of the rim gutter 16 and its associated side walls. The wipe 1 now sits on the top of the beverage can 2 with its inside face 99 touching or adjacent the beverage can's upper end surfaces.

The fingers in the hand holding the wipe 1 are placed in a partial ring on the wipe 1 and slight pressure is applied to the upper sidewall 60 and lower flared sidewall 62 so that they both firmly contact the top end of the can's side from the crimp ring 14, upper band 45 and upper skirt 4. The can 2 and wipe 1 are counter rotated (twisted in different directions with two hands) back and forth for bout 1-2 seconds. The fingertips of the wipe hand then exert downward pressure on the central dome 50 of the wipe 1 ensuring that the inner face 99 of the wipe 1 under the dome 50 and under the peripheral ring 52 contact the top end wall 8 the door 18 and the pull tab 17 of the can 2 while the can hand rotates the can back and forth. Again, this lasts for 1-2 seconds. Lastly, the index finger and thumb of the wipe hand pinch the rolled top edge 56 of the upper pleat fold 58 so as to wipe down onto the crimp ring 14 of the can while the can hand rotates the can back and forth for 1-2 seconds. At these wiping interfaces, the sanitizing fluid is transferred to the surfaces of the beverage can 2. After these steps the can is allowed to momentarily rest giving time for the sanitizing solution to evaporate. At this time, any additional cans may be sanitized as well using the initial wipe. Note, that groupings of beverage cans may be sanitized while still constrained by a conventional six-pack ring.

While the preferred embodiment uses a natural sanitizing fluid such as an acidic fruit juice, (preferably lime juice) in alternate embodiments antibacterial agents such as silver, copper, zinc, tin, or the like may optionally be incorporated into a sanitizing fluid such as alcohol, or into the wipe's material to enhance or maintain sterility. The series of embodiments provided herein, provide superior sanitization compared to the prior art because of the number of wiping faces incorporated and the individual pack The material of construction for the wipe 2 is a polymer it may have antibacterial agents such as silver, copper, zinc, tin, or the like, optionally incorporated into its material to enhance or help maintain sterility. The sanitizing fluid may be sprayed onto the surface of the wipe to a determined level of saturation or preferably the wipes will be fully immersed in the sanitizing fluid and allowed to drip dry to a specified level prior to encapsulation.

While certain features and aspects have been described, one skilled in the art will recognize that numerous modifications are possible. Consequently, although several exemplary embodiments are described above, it will be appreciated that the invention is intended to cover all modifications and equivalents within the scope of the following claims.

Having thus described the invention, what is claimed as new and desired to be secured by Letters Patent is as follows:

1. A beverage can sanitizing wipe, comprising:
    an airtight sealed polymer packaging;
    a circular polymer fabric wipe that is heat and vacuum formed into a three dimensional configuration having a central dome transitioning about its perimeter into a double pleat, said double pleat transitioning into an upper sidewall that angles into a flared sidewall with an outer bottom flange, said polymer fabric wipe having a brushed inner face and an outer face;
    a sanitizing fluid impregnated onto said brushed inner face of said polymer fabric wipe; and wherein-said polymer fabric wipe is contained within said airtight sealed polymer packaging.

2. The beverage can sanitizing wipe of claim 1 wherein said sanitizing fluid is a natural sanitizing fluid selected from the set of natural sanitizers consisting of lime juice, lemon juice, white vinegar, alcohol, vodka, hydrogen peroxide and essential oils including but not limited to tea tree, citronella, geranium, lemongrass, orange, and patchouli.

3. The beverage can sanitizing wipe of claim 2 wherein said polymer fabric wipe is a porous, non-woven filament fiber polyester selected from the group of polyesters comprising natural polyesters, synthetic polyesters or polyester blends.

4. The beverage can sanitizing wipe of claim 1 wherein said airtight sealed polymer packaging has a press actuated resealable closure affixed at an end of said packaging.

5. A beverage can sanitizing wipe, comprising:
    an airtight sealed polymer packaging;
    a circular polymer fabric wipe having that is heat and vacuum formed into a three dimensional configuration that has six distinct wiping faces;

a sanitizing fluid impregnated onto said polymer fabric wipe; and wherein-said polymer fabric wipe is contained within said airtight sealed polymer packaging.

* * * * *